(12) United States Patent
Mori et al.

(10) Patent No.: US 7,276,594 B1
(45) Date of Patent: Oct. 2, 2007

(54) NUCLEIC ACID-CONTAINING COMPLEX

(75) Inventors: Hidezo Mori, Tokyo (JP); Yasuhiko Tabata, Kyoto (JP); Kiyoshi Ando, Kanagawa (JP); Etsuro Tanaka, Kanagawa (JP); Harukazu Iseki, Kanagawa (JP); Hiromi Sakamoto, Chiba (JP); Naoto Fukuyama, Kanagawa (JP); Hirofumi Kasahara, Kanagawa (JP)

(73) Assignee: CMIC Company, Ltd., Tokyo (JP)

( * ) Notice: Subject to any disclaimer, the term of this patent is extended or adjusted under 35 U.S.C. 154(b) by 471 days.

(21) Appl. No.: 10/129,906

(22) PCT Filed: Nov. 9, 2000

(86) PCT No.: PCT/JP00/07882

§ 371 (c)(1),
(2), (4) Date: Oct. 28, 2002

(87) PCT Pub. No.: WO01/34206

PCT Pub. Date: May 17, 2001

(30) Foreign Application Priority Data

Nov. 9, 1999  (JP) ............................... 11-318187
Sep. 13, 2000 (JP) .............................. 2000-278878

(51) Int. Cl.
*C07H 21/04* (2006.01)
*A61K 9/14* (2006.01)

(52) U.S. Cl. ...................................... 536/23.5; 424/484
(58) Field of Classification Search ................... None
See application file for complete search history.

(56) References Cited

U.S. PATENT DOCUMENTS 5,294,249 A * 3/1994 Luisi ....................... 106/145.1
6,025,337 A * 2/2000 Truong et al. ................ 514/44

FOREIGN PATENT DOCUMENTS

WO    WO98/01162 A    1/1998

OTHER PUBLICATIONS

Konishi et al (J. Clin. Invest. 96(2): 1125-1130, 1995).*
Quong and Neufield, DNA encapsulation within co-guanidine membrane coated alginate beads and protection from extracapsular nuclease. Journal of Microencapsulation, 16:573-585, 1999.

* cited by examiner

*Primary Examiner*—Richard Schnizer
(74) *Attorney, Agent, or Firm*—Foley & Lardner, LLP

(57) ABSTRACT

A nucleic acid-complex, containing a nucleic acid and a positively charged, water-insoluble biodegradable polymer, is disclosed. The complex has properties of sustainedly releasing a desired nucleic acid, especially DNA, to a site. The complex can be taken up by phagocytes such as macrophages and delivered to a target site, allowing the function of the nucleic acid to be exhibited in a target specific manner.

2 Claims, 12 Drawing Sheets

Residual Radioactivity in Mouse Muscle

—●— Radioiodinated Particulate Aminated Gelatin Hydrogel Itself
—○— Particulate Aminated Gelatin Hydrogel Conjugated Radioiodinated DNA
—△— Aqueous Solution of Radioiodinated DNA

A x 80

B x 5

C x 50

X 25

X 5

X-axis FITC、Y-axis CD1a+CD83 (PE) = DC marker
LL=0%、UL=14%、UR=48%、LR=37%

NUCLEIC ACID-CONTAINING COMPLEX

BACKGROUND OF THE INVENTION

1. Field of the Invention

This invention relates to a nucleic acid-containing complex characterized by containing a nucleic acid, and a positively-charged water-insoluble biodegradable polymer, and also relates to a method for controlling the rate of release of the nucleic acid from the complex.

The invention is also concerned with phagocytic cells (hereinafter referred to as phagocytes) comprising a nucleic acid-containing complex containing a nucleic acid and a biodegradable polymer. The invention also concerns a drug having the nucleic acid-containing complex as an active ingredient and usable for phagocyte-mediated gene therapy.

2. Description of the Related Art

In recent years, as molecular genetic factors of human diseases have become clear, more and more emphasis has been placed on studies of gene therapy. Gene therapy is aimed at expressing DNA at a targeted site or cell. For this therapy, it would be beneficial to bring the DNA directly to the target site or cell, transfer it into the target site or cell efficiently, and express it at the specific site or in the cell functionally. Various methods have been reported for the effective transfer and expression of foreign DNA (Fumimaro Takaku, eds. "Idenshichiryo no Saizensen: Kisogijutu kara Rinsho Oyo made (The Forefront of Gene Therapy, from Basic Technology to Clinical Applications)", Experimental Medicine, Vol. 12, No. 15, 1994; Robert E. Sobol and Kevin J. Scanlon, The Internet Book of Gene Therapy, Appleton & Lange Stamford, Conn., 1995). They are roughly classified into (1) physical methods for DNA transfer (microinjection, electroporation), (2) chemical methods for DNA transfer (calcium phosphate transfection, DEAE-dextran transfection), and (3) biological methods (virus vectors, such as retroviruses and adenoviruses). The existing chemical methods, such as calcium phosphate transfection, and DEAE-dextran transfection, are generally low in the efficiency of gene transfer. The physical methods, such as microinjection and electroporation, may require special devices, and they are not practical for routine clinical use. Virus vectors have been expected to find clinical applications because of their high efficiency of gene transfer. However, these vectors involve the risk of adverse reactions such as immune reactions, due to their nature as viruses.

To overcome the above drawbacks, new technologies have been developed. Liposome methods incorporate gene into liposomes to protect the gene from inactivation or degradation. The liposomes are free from viral DNA, and thereby rule out the possibility that potentially dangerous recombination events may occur. However, their potent toxicity to a variety of cell types restricts the use of liposomes as carriers of DNA. Development of new substances and means for gene delivery continues even now.

In the field of gene therapy for vascular lesions, the so-called hydrogel method has also been developed which comprises adhering a hydrogel to the surface of a catheter to be introduced into a blood vessel, placing a plasmid gene in the hydrogel, and directly coating the hydrogel into the blood vessel (Marchall, E., Science, 269, 1050–1055, 1995). According to this method, the plasmid is slowly released from the hydrogel by simple diffusion. With this method, in general, both the period of slow release is brief, and this period is difficult to control both with respect to rate and length. Gene therapy requires that the amount of the therapeutic gene or the period of its supply be adjusted depending on the disease to be treated or the status of the disease. Thus, there is a demand for a method capable of controlling the period of slow release of the therapeutic gene according to the requirements of therapy.

When a foreign gene is to be used in a clinical setting such as gene therapy, a persistent supply of this gene at a stable level to the target site is necessary for the functional expression of the gene.

Furthermore, studies of gene therapies using antisense oligonucleic acids have attracted attention in recent years. Means for supplying such nucleic acids site-specifically and stably in vivo for controlled periods of time should enhance the efficacy of such an approach.

SUMMARY OF THE INVENTION

It is an object of the present invention to provide a nucleic acid-containing complex which is safe, has a high efficiency of introducing the nucleic acid into cells, and can persistently supply a nucleic acid to a target site, along with providing a method for controlling the rate of release of the nucleic acid from the nucleic acid-containing complex.

It is another object of the invention to provide a nucleic acid-containing complex which is safe, easy to handle, and excels in site-specific functional expression in vivo, along with a method which can exhibit the function of nucleic acid specifically to the target site with the use of the nucleic acid-containing complex.

As used herein, the phrase "the function of nucleic acid" refer to the expression of a gene which is encoded in the nucleic acid, but it can also refer to nucleic acids which exert a direct effect. Examples of nucleic acids exerting a direct effect include antisense nucleotides (Robert E. Sobol and Kevin J. Scanlon, The internet book of gene therapy, Appleton & Lange Stamford, Conn., 1995), ribozymes (U.S. Pat. No. 6,127,173), double-stranded DNA molecules which can function as decoys (Sobol, supra), and DNA/RNA hybrids (Bartlett et al., (2000) Nat. Biotech 18:615).

In light of these objectives, the inventors of this invention conducted extensive studies and obtained findings listed below. Fist, by complexing a negatively-charged nucleic acid and a positively-charged water-insoluble biodegradable polymer to form a stable complex, degradation of the nucleic acid in vivo can be suppressed, and the nucleic acid can be released at a sustained rate at the desired target site or cell. Second, a complex obtained by complexing a nucleic acid with a biodegradable polymer, like the nucleic acid-containing complex described herein, is easily taken into phagocytes which play important roles in the immune system (first, targeting the complex to phagocytes). The phagocytes taking up the complex migrate to a target site (second, targeting the phagocytes to the target site), and therefore the phagocytes increase the efficacy of the technique by targeting the effect of the added nucleic acid to the target site. Based on these findings, the inventors accomplished the present invention.

In one aspect the invention features a nucleic acid-containing complex, containing a nucleic acid and a positively-charged water-insoluble biodegradable polymer, wherein the nucleic acid can be released via degradation of the biodegradable polymer.

In another aspect the invention features a nucleic acid-containing complex, containing a nucleic acid and a positively-charged water-insoluble biodegradable polymer having a positively-charged group added to the polymer.

In the nucleic acid-containing complex of the invention, the positively-charged water-insoluble biodegradable polymer contains at least one member selected from the group consisting of collagen, gelatin, chitin, chitosan, hyaluronic acid, alginic acid, starch, and derivatives of any of these substances. Preferably, the derivatives are amino derivatives.

In a preferred embodiment, the positively-charged water-insoluble biodegradable polymer is crosslinked gelatin having an introduced positively-charged group. In another preferred embodiment, the nucleic acid is at least one member selected from the group consisting of a plasmid DNA, an oligonucleotide, and a double-stranded nucleic acid compound.

In a preferred embodiment, the nucleic acid encodes a polypeptide which comprises at least one member selected from the group consisting of vascular endothelial growth factor gene, hepatocyte growth factor gene, and fibroblast growth factor gene, as well as other genes such as kinases, phosphatases, transcription factors, cytokines, proteases, apoptosis-inducing factors and apoptosis-retarding factors. More preferably, the DNA comprises a base sequence described as SEQ. ID No. 1 of the sequence listing which encodes FGF4/HST1.

In another aspect the invention features a pharmaceutical composition comprising the nucleic acid-containing complex of the instant invention as an active ingredient. In a preferred embodiment, the pharmaceutical composition is used for gene therapy, especially where the gene therapy is effected by a local administration of the gene.

In yet another aspect the invention features a method for controlling a rate of nucleic acid release, characterized by incorporating a nucleic acid into a positively-charged water-insoluble biodegradable polymer, and releasing the nucleic acid by degradation of the biodegradable polymer.

In another aspect the invention features a method for controlling a rate of nucleic acid release, characterized by incorporating a nucleic acid into a positively-charged water-insoluble biodegradable polymer having an introduced positively-charged group, and releasing the nucleic acid by degradation of the biodegradable polymer.

In another aspect the invention features a method for enhancing functional expression of a nucleic acid, characterized by incorporating the nucleic acid into a positively-charged water-insoluble biodegradable polymer, and releasing the nucleic acid by degradation of the biodegradable polymer to exhibit the function of the nucleic acid. The invention also features a method for enhancing functional expression of a nucleic acid, characterized by incorporating the nucleic acid into a positively-charged water-insoluble biodegradable polymer having an introduced positively-charged group, and releasing the nucleic acid by degradation of the biodegradable polymer to exhibit the function of the nucleic acid.

In a preferred embodiment, the positively-charged water-insoluble biodegradable polymer has at least one member selected from the group consisting of collagen, gelatin, chitin, chitosan, hyaluronic acid, alginic acid, starch, and derivatives of any of these substances (e.g., amino derivatives). Preferably, the positively-charged water-insoluble biodegradable polymer is crosslinked gelatin having an introduced positively-charged group. The nucleic acid is at least one member selected from the group consisting of a DNA encoding a gene, an oligonucleotide, and a double-stranded nucleic acid compound. The nucleic acid may encode vascular endothelial growth factor gene, hepatocyte growth factor gene, and fibroblast growth factor gene, as well as other genes such as kinases, phosphatases, transcription factors, cytokines, proteases, apoptosis-inducing factors and apoptosis-retarding factors. In a preferred embodiment, a DNA molecule comprising a base sequence described as SEQ. ID No. 1 of the sequence listing.

In yet another aspect the invention features a phagocyte comprising a nucleic acid-containing complex which contains a nucleic acid and a biodegradable polymer. In a preferred embodiment, the biodegradable polymer has at least one member selected from the group consisting of collagen, gelatin, chitin, chitosan, hyaluronic acid, alginic acid, starch, and derivatives of any of these substances.

In yet another aspect the invention features a method for exhibiting a function of a nucleic acid at a target site, at least including the steps of (i) allowing phagocytes to take up a nucleic acid-containing complex containing the nucleic acid and a biodegradable polymer, (ii) allowing the taken up nucleic acid to exert its function or inducing the expression of the nucleic acid in the phagocytes, and delivering the phagocytes to the target site. Preferably, the biodegradable polymer is at least one member selected from the group consisting of collagen, gelatin, chitin, chitosan, hyaluronic acid, alginic acid, starch, and derivatives of any of these substances.

In yet another aspect the invention features a pharmaceutical composition for gene therapy, containing a nucleic acid-containing complex as an active ingredient, the nucleic acid-containing complex containing a nucleic acid and a biodegradable polymer, wherein the gene therapy at least includes the steps of (i) allowing phagocytes to take up the nucleic acid-containing complex containing the nucleic acid and the biodegradable polymer, (ii) allowing the taken up nucleic acid to exert its function or inducing the expression of the nucleic acid in the phagocytes, and (iii) delivering the phagocytes to a target site. In a preferred embodiment, the biodegradable polymer has at least one member selected from the group consisting of collagen, gelatin, chitin, chitosan, hyaluronic acid, alginic acid, starch, and derivatives of any one of these substances.

BRIEF DESCRIPTION OF THE DRAWINGS

FIG. 4A: Particulate aminated gelatin hydrogel-conjugated lacZ plasmid (lacZ plasmid: 500 µg). FIG. 4B: Naked lacZ plasmid (500 µg) not conjugated to particulate aminated gelatin hydrogel. FIG. 4C: Particulate aminated gelatin hydrogel-conjugated lacZ plasmid (lacZ plasmid: 50 µg).

FIG. 5A: Three days after administration of lacZ gene. FIG. 5B: Two weeks after administration of lacZ gene.

FIG. 6A: Particulate aminated gelatin hydrogel-conjugated FGF4/HST1 plasmid (500 μg). FIG. 6B: Particulate aminated gelatin hydrogel-conjugated FGF4/HST1 plasmid (5 μg). FIG. 6C: Particulate aminated gelatin hydrogel-conjugated lacZ plasmid (500 μg). FIG. 6D: Naked FGF4/HST1 plasmid (500 μg) not conjugated to particulate aminated gelatin hydrogel.

FIG. 10A shows a phase contrast image, while FIG. 10B shows a fluorescence image in the same field as in FIG. 10A. Fluorescence is observed in macrophages, showing that crosslinked gelatin particles-GFP plasmid has been incorporated into macrophages.

FIG. 11A: The results for DC cultured together with particulate aminated gelatin hydrogel-conjugated GFP plasmid. FIG. 11B: The results for DC cultured together with naked GFP plasmid.

DETAILED DESCRIPTION OF THE PREFERRED EMBODIMENTS

Figure 1:
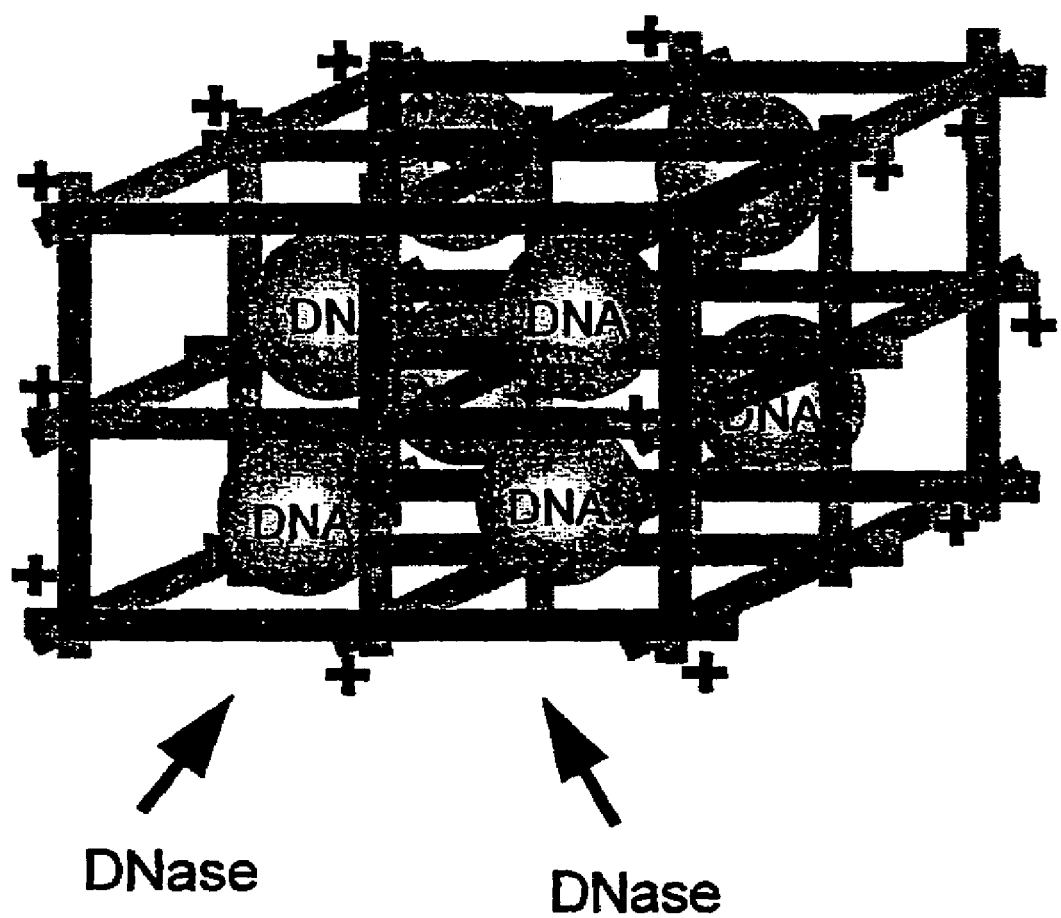
FIG. 1 is a schematic view showing ionic bonding of a three-dimensional lattice of a gelatin hydrogel and plasmid DNA's.

The nucleic acid that can be incorporated into the complex of the invention is not restricted. However, preferred embodiments are nucleic acids whose introduction brings a therapeutic effect, and they are selected, as desired, according to the purpose of use of the complex. In the invention, antisense oligonucleotides for certain genes, and double-stranded nucleic acid compounds, such as decoy nucleic acids, can be used preferably in addition to various DNAs encoding a gene (Sobol, supra). Nucleic acid constructs can also be delivered to correct point mutations (Bartlett et al. (2000) Nat. Biotech 18:615). More concretely, nucleic acids which can be incorporated into the nucleic acid-containing complex of the invention for gene therapy in the cardiovascular field as well as gene therapy of cancer are listed in Table 1 along with their therapeutic aim. However, the invention is not restricted to them, and the invention is applicable to other clinical fields, as known by those skilled in the art.

TABLE 1

| | Purpose | Type of nucleic acid |
|---|---|---|
| Gene therapy in cardio-vascular field | Enhances vasculogenesis and applicable to obstructive arteriosclerosis and ischemic heart disease | Vascular endothelial growth factor (VEGF) gene<br>Hepatocyte growth factor (HGF) gene<br>Fibroblast growth factor (FGF) gene |

TABLE 1-continued

| | Purpose | Type of nucleic acid |
|---|---|---|
| | Regenerates vascular endothelial cells and applicable to prevention of restenosis following arterioplasty | VEGF gene<br>HGF gene<br>Endothelial nitric oxide synthase gene<br>$PGI_2$ synthetic gene |
| | Regulates cell cycle of vascular smooth muscle cells and usable for prophylaxis of restenosis following arterioplasty or bypass operation | Antisense oligonucleotide to C-myb<br>Antisense oligonucleotide to PCNA gene<br>Antisense oligonucleotide to cdc-2 kinase |
| | Usable for prophylaxis, etc. of restenosis following bypass operation | Double stranded nucleic acid compound having the same sequence as transcription factor E2F conjugated sequence E2F decoy |
| | Applicable to gene therapy for ischemia-reperfusion injury | NFKB decoy |
| Gene therapy for cancer | Suicide gene transfer | Herpes simplex virus-thymidine kinase gene |
| | Tumor suppressor gene transfer | p53 gene |
| | Protection of bone marrow stem cells from anticancer drug | Multidrug resistance (MDR) gene |
| | Immunotherapy | Interleukin 12 gene<br>B7 gene |
| | Antisense RNA | ras gene |

Preferred examples of the nucleic acids to be incorporated into the nucleic acid-containing complex of the invention are vascular endothelial growth factor gene, hepatocyte growth factor gene, and fibroblast growth factor gene. Other such genes are known to those skilled in the art including kinases, phosphatases, transcription factors, cytokines, proteases, apoptosis-inducing factors and apoptosis-retarding factors. As an example of the fibroblast growth factor gene, FGF4/HST1 gene having a base sequence described as SEQ. ID No. 1 of the sequence listing can be cited.

The FGF4/HST1 gene was isolated and identified as a gene having the activity of transforming NIH3T3 cells (hst-1; Proc. Natl. Acad. Sci. USA, 83:3997–4001, 1986). Then, this gene was found to have homology to fibroblast growth factor (FGF), and became the fourth member of the FGF family (FGF4). Currently, 20 members of the FGF family, FGF 1 to 20, are known.

FGF4/HST1 protein is a secretory protein having a signal peptide, and has been reported to have the following activities: Cell growth promotion for fibroblasts and vascular endothelial cells; vasculogenesis; promotion of growth and differentiation of megakaryocytes; promotion of secretion of cytokines from megakaryocytes; promotion of adhesion between megakaryocytes and endothelial cells; in vitro induction of increases in peripheral platelet count; alleviation of platelet decreases and shortening of convalescence by prior administration in thrombopenic models due to chemotherapy or radiotherapy; and increases in survival rates following lethal radiation dose by prior administration.

As the application of the FGF4/HST1 gene to gene therapy, an attempt has been made to apply an adenovirus vector, into which this gene has been integrated, to the treatment of chronic stable angina pectoris due to arteriosclerosis (Collateral Therapeutics).

In the instant invention, the nucleic acid is used in a form in which it is introduced into cells, and can exhibit its function in the cells. In the case of DNA, for example, it is used as a plasmid having the DNA located therein so that the DNA will be transcribed in cells in which it has been introduced, then a polypeptide encoded by the DNA will be produced, and then the desired function will be exhibited by the polypeptide. Preferably, a promoter region, an initiation codon, DNA coding for a protein having the desired function, a termination codon, and a terminator region are continuously arranged in the plasmid. Such techniques and DNA elements are well known to those skilled in the art.

If desired, two or more nucleic acids can be incorporated into one plasmid. Also, if desired, two or more nucleic acids may be separately joined to a water-insoluble biodegradable polymer (as described below) to form one nucleic acid-containing complex.

Conveniently, the intended vector can be prepared by inserting the desired nucleic acid into a plasmid, which is available in the art, with the use of a suitable restriction enzyme site. It is also possible to prepare the vector by synthetic means or semisynthetic means on the basis of the base sequence of the nucleic acid to be introduced. Such techniques are well known to those skilled in the art. Techniques such as those set forth in "Molecular Cloning: A Laboratory Manual", second edition, Cold Spring Harbor Laboratory, Sambrook, Fritsch & Maniatis, eds., 1989, which is incorporated herein by reference in its entirety including any figures, tables or drawings.

In the invention, "cells" into which the nucleic acid is introduced are preferably cells in which the functional expression of the nucleic acid is required, as well as cells having the feature of taking up substances outside the cell (i.e., phagocytosis). In preferred embodiments, these cells are phagocytes such as macrophages, which are described below. The cells in which the functional expression of the nucleic acid should be exhibited are selected variously, for example, depending on the nucleic acid used (i.e., its function). Examples are myocardial cells, skeletal muscle cells, and vascular endothelial cells. Phagocytes, such as monocytes, dendritic cells, macrophages, histiocytes, Kupffer cells, osteoclasts, synovial A cells, microglial cells, Langerhans' cells, epithelioid cells, and multinucleate giant cells; leucocytes; fibroblasts; and certain epithelia cells (gastrointestinal epithelial cells, renal tubular epithelial cells) can efficiently take the nucleic acid-containing complex into their interior by their phagocytosis (first, targeting the nucleic acid-containing complex to phagocytes), and are favorable in delivering the nucleic acid to the desired site by their propensity to migrate in vivo (second, targeting phagocytes to target sites and cells). Hence, every organ or tissue, such as heart, muscle, blood vessel, blood, bone marrow, lymphatic tissue, connective tissue, liver, bone, synovial membrane, nerve, skin, inflammatory tissue, or cancer tissue, can be affected by gene therapy.

In the invention, "biodegradable polymer" refers to a polymer which is hydrolyzed for the first time by the action of a physiologically active substance present in vivo, for example, an enzyme. Examples of the biodegradable polymer are polysaccharides, such as chitin, chitosan, hyaluronic acid, alginic acid, starch, and pectin, proteins such as gelatin, collagen, fibrin and albumin, and derivatives of these. A preferred example is gelatin or its derivative. For the purpose of this specification, "biodegradable polymer" does not include nucleic acids. In the invention, "degradation of the biodegradable polymer" refers to the hydrolysis of the polymer by the action of a physiologically active substance present in vivo, such as an enzyme, or by its in vivo non-enzymatic action, as stated above.

Here, "the derivative" refers to a modified form of the biodegradable polymer suitable for formation of the nucleic acid-containing complex, and includes, for example, an amino derivative having an amino group introduced onto the polymer as will be described below.

In the invention, if more controlled release of the nucleic acid from the nucleic acid-containing complex is desired, the biodegradable polymer that forms the complex with the nucleic acid is preferably water-insoluble. Here, the water-insoluble property refers to the nature of not dissolving in water because of chemical or physical crosslinking between the molecules. In accordance with the stipulations of the Japanese Pharmacopoeia, the water-insoluble property corresponds to "sparingly soluble" to "practically insoluble".

The biodegradable polymer is not restricted to a certain set of molecules, as long as it can form a complex with nucleic acid. If sustained release is desired, the polymer should preferably be charged positively so that a stable nucleic acid-containing complex will be formed. The degree of the positive charge is varied so as to allow a polyion to form a complex with a normally negatively charged nucleic acid. The formation of the polyionic complex can be confirmed by measuring an increase in the turbidity of a mixture obtained by mixing in water the components present in the water-soluble state.

The strong binding (ionic bonding) between the negative charge of the nucleic acid and the positive charge of the biodegradable polymer results in the formation of a stable nucleic acid-containing complex. If a biodegradable polymer which is neutral or only slightly positively charged is used in the invention, the polymer may be made cationic by introducing an amino group or the like therein beforehand. Even in an already positively-charged biodegradable polymer, a positively-charged group, such as an amino group, may be introduced. By so doing, the positive charge of the overall molecule is enhanced, and binding to the nucleic acid increases, so that a more stable nucleic acid-containing complex can be formed. The cation-imparting procedure can be performed by methods known to those skilled in the art.

The cation-imparting process is not restricted, as long as such a process can introduce a functional group which will be cationic under physiological conditions. A preferred method is to introduce an amino group or an ammonium group onto a hydroxyl group or a carboxyl group, already part of the biodegradable polymer, under mild conditions. An example of the method comprises reacting the polymer with an alkyldiamine, such as ethylenediamine or N,N-dimethyl-1,3-diaminopropane, trimethylammonium acetohydrazide, spermine, spermidine, or diethylamidochloride, with the use of any of various condensing agents, e.g., 1-ethyl-3-(3-dimethylaminopropyl)carbodiimide hydrochloride, cyanuric chloride, N,N'-carbodiimidazole, cyanogen bromide, diepoxy compound, tosyl chloride, a dianhydride compound such as diethyltriamine-N,N,N',N'',N''-pentanoic acid dianhydride, or trityl chloride. In a preferred embodiment, the method involves a reaction with ethylenediamine as it is convenient and versatile.

In the invention, the step of "introducing a positively-charged group" refers to the introduction of a functional group which makes the biodegradable polymer cationic under physiological conditions. It means to introduce the above-mentioned functional group onto the biodegradable polymer.

In the invention, moreover, it is preferred to make the biodegradable polymer water-insoluble by a crosslinking treatment or other similarly effective treatments for the purpose of enabling controlled release of nucleic acid. Generally, many biodegradable polymers are water soluble, and thus the resulting nucleic acid-containing complex is also water soluble. When this complex is administered in vivo, the nucleic acid is rapidly released from the complex, thus it is difficult to obtain stable local and sustained supply of the nucleic acid. The instant invention uses a water-insoluble biodegradable polymer, making it possible to release nucleic acid in a controlled fashion in accordance with the degradability of the biodegradable polymer in vivo. That is, the sustained rate of release the nucleic acid can be controlled according to the degradation of the biodegradable polymer. Furthermore, the sustained release form permits the increase in the efficiency of local expression of gene by the nucleic acid-containing complex.

In preferred embodiments, the water-insoluble biodegradable polymer used in the invention is a gelatin hydrogel insolubilized in water by crosslinking. In more preferred embodiments, a gelatin hydrogel has a water content of 85%, 88%, 91%, 94%, 95%, 97%, 99% or more.

Crosslinking of the biodegradable polymer can be performed by methods known to those skilled in the art. Examples are methods using crosslinking agents, heat treatment, and methods using ultraviolet radiation.

Preferred crosslinking agents may be selected according to the type of the biodegradable polymer used. Normally, the following crosslinking agents are used: formalin, glutaraldehyde, water soluble carbodiimides [1-ethyl-3-(3-dimethylaminopropyl)carbodiimide hydrochloride, 1-cyclohexyl-3-(2-morpholinoethyl)carbodiimide-metho-p-toluenesulfonate, etc.], epichlorohydrin, and diepoxy compounds [bisepoxydiethylene glycol, 1,4-bis-(2,3-epoxypropoxy)-butane, etc.]. In the crosslinking reaction, the concentration of the biodegradable polymer is 1 to 30% by weight, preferably 5 to 10% by weight, while the concentration of the crosslinking agent is $10^{-3}$ to 10% by weight, preferably $10^{-2}$ to 1% by weight. The reaction is performed for 1 to 48 hours, preferably 12 to 24 hours, at 0 to 40° C., preferably 25 to 30° C.

Crosslinking of the biodegradable polymer can also be performed by heat treatment. The method of thermal crosslinking will be described in the examples below, with gelatin taken as an example.

An aqueous solution of gelatin (preferably, about 10% by weight) is cast into a plastic petri dish, and air dried to obtain a gelatin film. The film is allowed to stand for 1 to 48 hours, preferably for 6 to 24 hours, at a temperature of between 110 and 160° C., preferably 120 and 150° C., under reduced pressure, preferably of about 10 mmHg, whereby the film is thermally crosslinked.

When the gelatin film is to be crosslinked with ultraviolet rays, the gelatin film is allowed to stand, normally, at 0 to 40° C., and preferably at room temperature, below a germicidal lamp.

The gelatin used may be a mixture of gelatins having different physical properties, such as solubility, stability, and swelling properties. A mixture of crosslinked gelatins different in physical properties may also be used.

The positively-charged water-insoluble biodegradable polymer incorporated in the nucleic acid-containing complex of the invention may be incorporated in the complex in the following manner: the biodegradable polymer having the above-mentioned characteristics is incorporated alone, or two or more types of the biodegradable polymers are incorporated as a mixture (simply mixed to be incorporated in the same nucleic acid-containing complex). Alternatively, two or more types of the biodegradable polymers may be chemically bonded beforehand, and then incorporated in the complex. Any of these embodiments are included in the invention.

To chemically bond two or more types of the biodegradable polymers beforehand, and incorporate the bonding product in the complex, the respective biodegradable polymers can be separately made water-insoluble, and then chemically bonded, or can be chemically bonded, and then made water-insoluble. In preferred embodiments, the respective biodegradable polymers are first bonded chemically, and then treated to render them water-insoluble.

In the invention, the complex containing nucleic acid and a positively-charged water-insoluble biodegradable polymer can be prepared easily by mixing the aforementioned nucleic acid and the aforementioned positively-charged water-insoluble biodegradable polymer. The ratio between the amounts of the nucleic acid and the positively-charged water-insoluble biodegradable polymer differs according to the degree of positive charge of the biodegradable polymer used. Usually during the mixing, the nucleic acid is used at a saturating concentration with respect to the biodegradable polymer.

In a preferred embodiment for preparing a nucleic acid-containing complex containing a nucleic acid in a crosslinked gelatin gel, a crosslinking agent is directly added to an aqueous solution of gelatin of between 5% to 30% by weight to prepare a crosslinked gelatin gel. In a more preferred embodiment, an uncrosslinked gelatin gel is dipped in an aqueous solution of a crosslinking agent to prepare a crosslinked gelatin gel. The resulting crosslinked gelatin gel is then directly dipped in a solution containing nucleic acid. In a preferred embodiment, the crosslinked gelatin gel is dried, and then swollen again in a solution containing nucleic acid.

The strongly negatively charged nucleic acid is ionically bonded to the positively-charged biodegradable polymer to form a complex. In such a complex of the instant invention, the nucleic acid incorporated in the complex is characterized by being released from the complex by degradation of the biodegradable polymer by the action of an enzyme, or other physiological processes. FIG. 1 shows a schematic view of the complex, with DNA taken as an example of the nucleic acid.

In complexing the nucleic acid, other components may be added, if desired, for purposes such as stability of the resulting nucleic acid-containing complex, sustained release of the nucleic acid, and functional expression of the released nucleic acid. Examples of these other components are aminosugars or their macromolecular compounds or chitosan oligomers, basic amino acids or their oligomers or macromolecular compounds, and basic polymers such as polyallylamine, polydiethylaminoethylacrylamide, and polyethyleneimine. Furthermore, ligand proteins capable of binding to receptors expressed in an organ specific fashion, or antibodies directed specifically to selected targets are added, thereby making possible the delivery of the nucleic acid-containing complex to the desired site, and eventually, the localized release of the nucleic acid. Such ligands and/or antibodies are well known to one skilled in the art.

The invention also relates to a method for controlling a rate of nucleic acid release, characterized by incorporating a nucleic acid into a positively-charged water-insoluble biodegradable polymer, and allowing the release of the nucleic acid in a physiological setting.

As the nucleic acid and the positively-charged water-insoluble biodegradable polymer used in the method for controlling a rate of nucleic acid release according to the invention, all those biodegradable polymers and nucleic acids named herein may be used, as well as others known to one those skilled in the art.

The nucleic acid incorporated in the complex is slowly released from the complex as the water-insoluble biodegradable polymer is degraded in vivo (in other words, the degradation rate determines the rate of release). This release is preferably effected only through the mediation of the biodegradable polymer, because that would be able to control the rate of release more reproducible. The rate of release is closely related to the strength of bonding between the nucleic acid and the biodegradable polymer in the complex, along with the stability of the complex, in addition to the degree of biodegradability of the biodegradable polymer used (which in turn can depend on the water content of the biodegradable polymer). The rate of release can also be controlled by the balance between the positive charge and the negative charge in the complex. Usually, the higher the positive charge of the biodegradable polymer used, the more the nucleic acid in the resulting nucleic acid-containing complex is retained. Thus, a biodegradable polymer with a higher positive charge is superior in terms of the controlled release of the nucleic acid via degradation of the water-insoluble biodegradable polymer. If the positive charge of the biodegradable polymer is insufficient to provide controlled release, an amino group or similar substituent is further introduced into the polymer to make the polymer cationic, thereby increasing its positive charge.

The invention also provides phagocytes comprising a nucleic acid-containing complex which contains a nucleic acid and a biodegradable polymer. This is based on the new finding that such a complex is readily taken into phagocytes which play important roles in the immune system (first, targeting of the complex at phagocytes), and the phagocytes are carried to a target site based on their normal, in vivo migration (second, targeting of the phagocytes at the target site), thus making it possible to exhibit the function of the nucleic acid readily and stably at the target site. The phagocytes used in the invention are not restricted, as long as they are cells exhibiting phagocytosis and which migrate to lesions (e.g., inflammatory sites, cancer tissue, etc.). For example, macrophages and monocytes are preferred examples of such cells. Also, dendritic cells, histiocytes, Kupffer cells, osteoclasts, synovial A cells, microglial cells, Langerhans' cells, epithelioid cells, and multinucleate giant cells are also preferred, even though their migration is minimal. The nucleic acid-containing complex containing the nucleic acid and the biodegradable polymer is readily taken into the phagocytes by the phagocytosis. The uptake of the nucleic acid-containing complex by the phagocytes can be performed in situ or in vitro according to the purpose of use.

As the nucleic acid and the biodegradable polymer incorporated into the nucleic acid-containing complex used, all those biodegradable polymers and nucleic acids listed herein may be used. The charge properties and solubility of the biodegradable polymer are not restricted. From the viewpoints of the ease of uptake by phagocytes, the uptake efficiency and the rate of uptake, the biodegradable polymer is preferably water-insoluble. From the viewpoint that firm bonding to the nucleic acid is desirable for reliable binding of the nucleic acid, the biodegradable polymer is preferably positively-charged. The terms "water-insoluble" and "positively-charged" are intended to have the same meanings as described earlier.

The phagocytes incorporating the nucleic acid-containing complex which contains the nucleic acid and the biodegradable polymer can be used for experimental purposes, and can also be used preferably as drugs. That is, phagocytes incorporating the nucleic acid-containing complex are prepared in vitro, and then the resulting phagocytes are administered in vivo, whereby desired genetic information from the nucleic acid can be expressed at the target site by making use of the phagocytes' characteristic accumulation at a lesion or other diseased site.

The invention also provides a method for exhibiting a function of a nucleic acid in a target site-specific manner, including at least the steps of (i) allowing phagocytes to take up the nucleic acid-containing complex containing the nucleic acid and a biodegradable polymer, (ii) inducing expression of the nucleic acid in the phagocytes, and (iii) delivering the phagocytes to the target site. Each of the steps will be described below.

(i) The Step of Allowing Phagocytes to Take Up a Nucleic Acid-Containing Complex Containing a Nucleic Acid and a Biodegradable Polymer:

This step, as has been described earlier, is achieved by the incorporation of the nucleic acid-containing complex into phagocytes by a phagocytic action inherent in the phagocytes. This step can be performed by mixing the nucleic acid-containing complex and phagocytes beforehand in vitro, or by administering the nucleic acid-containing complex in vivo and utilizing its uptake by phagocytes in vivo. The mixing ratio of the nucleic acid-containing complex to phagocytes in vitro is not restricted, and may be any ratio at which phagocytes can take in the nucleic acid-containing complex. Normally, the step is achieved by adding the nucleic acid-containing complex in an excess amount. The administration of the nucleic acid-containing complex in vivo, or the administration of in vitro prepared phagocytes under in vivo conditions can be performed in accordance with the mode of administration of the nucleic acid-containing complex and drug of the invention (described below). Such nucleic acid-containing complex phagocytes when prepared in vitro can also be considered a drug for the purposes of the instant invention. When administering the phagocytes of the invention which comprise the nucleic acid-containing complex into a living organism, it is necessary to perform administration while maintaining the viability and activity of the phagocytes. Methods complying with bone marrow transplantation or immunotherapy can be adopted, and are known to those skilled in the art. Preferably, typical examples of the methods for administration are as follows: (a) administration into a lesion or neighboring tissue; (b) administration into a body cavity (pericardial cavity, thoracic cavity, abdominal cavity, cerebrospinal cavity); (c) administration into a blood vessel or lymphatic tissue governing the lesion; (d) Administration into a blood vessel or dermal, adipose or skeletal muscle tissue apart from the lesion. Any of these administration methods can be expected to take effect at the site of lesion, rather than at the site of administration, because of the inherent migratory capacity of phagocytes.

(ii) The Step of Inducing Expression of the Nucleic Acid in Phagocytes:

This step is performed using a technique which is known to those skilled in the art. That is, the step is performed by incorporating the nucleic acid in a manner in which the nucleic acid can display its function in phagocytes when introduced into these cells. In preferred embodiments, the function of the incorporated nucleic acid is the expression of a gene encoded by the nucleic acid. In other preferred embodiments, the function of the nucleic acid may be by direct action of the nucleic acid incorporated in the complex. In the instant invention, the nucleic acid is taken into phagocytes as a nucleic acid-containing complex having the nucleic acid complexed with the biodegradable polymer. Hence, the sustained release of the nucleic acid controlled by the biodegradability of the nucleic acid-containing complex increases the efficiency of introduction of the nucleic acid into the cells, and promotes the expression or other function of the nucleic acid in the cells.

(iii) The Step of Delivering Phagocytes to the Target Site:

This step is performed easily and safely by the migration of phagocytes. Preferably, phagocytes are selected according to the desired target site. If targeting at cancer tissue or inflammatory tissue is desired, for example, macrophages, epithelioid cells, and multinucleate giant cells are preferably used. Monocytes are preferably used for blood targets; dendritic cells for targets in bone marrow and lymphatic tissue; histiocytes for targets in connective tissue; Kupffer cells for targets in the liver; osteoclasts for targets in the bone; synovial A cells for targets in the synovium; microglial cells for targets in the nervous system; and Langerhans' cells for targets in the skin. Furthermore, the administration of the phagocytes to the surfaces of various organs enables the nucleic acid (carried in the phagocytes) to be transported deep in the target organ.

The invention also provides a novel drug for gene therapy which utilizes the uptake of a nucleic acid-containing complex based on the phagocytosis of phagocytes, and which utilizes the delivery of the complex to the target site based on the inherent migratory capacity of the phagocytes, as detailed above. This drug has a nucleic acid-containing complex containing a nucleic acid and a biodegradable polymer as an active ingredient. The intended range of the components of the complex are described above and below.

The nucleic acid-containing complex of the invention can be administered in vivo by a variety of methods. For persistent and local release of the nucleic acid at the desired particular site, parenteral administration is particularly preferred. A drug containing the nucleic acid-containing complex of the invention as an active ingredient can be prepared by mixing the complex, if necessary, with pharmaceutically acceptable carriers (stabilizer, preservative, solubilizer, pH regulator, viscosity-increasing agent, etc.). These carriers are known to those skilled in the art. Various additives for adjusting the sustained release effect may further be incorporated and are known to those skilled in the art.

The drug having the nucleic acid-containing complex of the invention as the active ingredient also includes two or more types of nucleic acid-containing complexes containing different kinds of nucleic acids. Such a drug which has a plurality of therapeutic purposes is particularly useful in the field of gene therapy which has become diversified.

The nucleic acid-containing complex of the invention can be pharmaceutically manufactured in various forms according to the intended purpose. Examples of the forms are solid and semisolid preparations in the form of granule, cylinder or prism, sheet, disc, paste, etc., or injections such as suspensions and emulsions. Preferred are solid preparations having an excellent sustained release effect at the desired particular site, and preferred for local administration. For instance, the nucleic acid-containing complex of the invention prepared in a sheet form is suitable for fixing to the inner wall of a local blood vessel. More concretely, a method is available in which the sheet-shaped nucleic acid-containing complex is wound about a stent for arterioplasty, the stent is inserted into an appropriate blood vessel ramus by means of a catheter, and a balloon is inflated in the local blood vessel to fix the nucleic acid-containing complex to the inner wall of the blood vessel. This method enables gene transfer into a blood vessel wall at a site where the complex is fixed, and gene therapy for the region peripheral to the site of fixing. Preferred embodiments include gene therapy of cancer, such as anti-vasculogenesis therapy, or gene therapy of a circulatory disorder, such as vasculogenesis therapy.

The injections of the nucleic acid-containing complex can be administered intramuscularly, into adipose tissue, subcutaneously, intradermally, intravenously, into the lymphatic vessel, into the lymph node, intra-arterially, into a body cavity (pericardial cavity, thoracic cavity, abdominal cavity, cerebrospinal cavity), or into the bone marrow. The intramuscular administration is preferred. Direct administration into diseased tissue is also possible.

In the case of solid and semisolid preparations, the following methods are cited as examples: The preparation is directly embedded at a site where release of the nucleic acid is expected; A pasty preparation is injected by a syringe; A granular preparation is injected as a parenteral suspension; A catheter is inserted in a percutaneous, transluminal manner, and the complex adhered to a stent is self-retained in the blood vessel via the catheter; and fine particles of the complex (particle size: about several microns to about 15 microns) are injected through a catheter, and localized at a site where release of the nucleic acid is expected. These methods and others are known to those skilled in the art.

In pharmaceutically manufacturing the complex of the invention, it is further desirable to subject it to a sterilization step such as sterile filtration.

According to the invention, the dose administered in an animal, especially human, varies with various factors, such as the desired nucleic acid, the biodegradable polymer used, the mode of administration, and the particular site to be treated. However, the dose should be an amount sufficient to bring a therapeutic response. Such doses are known to those skilled in the art.

The nucleic acid-containing complex of the invention is applied, preferably, to gene therapy. Diseases to which the complex is applicable differ according to the type of the nucleic acid incorporated in the complex. Examples of the diseases are diseases in the cardiovascular field, such as peripheral arterial diseases, coronary arterial diseases, and diseases causing lesions, e.g., restenosis following arteriodilating operation. Other examples are cancer (malignant melanoma, intracranial tumor, metastatic malignant tumor, breast cancer, etc.), infections (HIV, etc.), and monogenic diseases (cystic fibrosis, chronic granulomatous disease, $\alpha_1$-antitrypsin deficiency, Gaucher disease, etc.).

In preferred embodiments, when a fibroblast growth factor gene, especially, DNA comprising a base sequence described as SEQ. ID No. 1 of the sequence listing, is used as a nucleic acid incorporated in the complex, it can be applied to various diseases against which the physiological activity of the aforementioned FGF4/HST1 protein is therapeutically effective.

EXAMPLES

Examples and Experimental Examples will be offered to illustrate the invention in more detail, but they in no way limit the invention.

Example 1

(1) Preparation of Aminated Gelatin

1 Gram of gelatin having an isoelectric point of 9.0 (Nitta Gelatin Company) was dissolved in 50 ml of 0.1 M phosphate buffer (PB, pH 5.0). Then, ethylenediamine (molecular weight: 60.1) in an amount of 50 mols, per mol of the carboxyl groups of the gelatin (molecular weight: 10,000, carboxyl group content: 95 mols/gelatin molecule), was added to the solution, and 1-ethyl-3-(3-dimethylaminopropyl)carbodiimide hydrochloride (molecular weight: 191.7) in an amount of 50 mols per mol of the carboxyl groups was further added. The resulting mixed solution was stirred for 12 hours at 37° C. Upon completion of the reaction, the reaction mixture was dialyzed against water for 2 days, and lyophilized to obtain aminated gelatin. Colorimetric quantitative analysis for amino groups with the use of sodium trinitrobenzenesulfonate showed that 56% of the carboxyl groups of the gelatin were aminated.

(2) Preparation of Particulate Aminated Gelatin Hydrogel

An aqueous solution (0.2 ml) of 100 mg/ml of the aminated gelatin that had been pretreated to 40° C. was charged into 5 ml of an olive oil. The mixture was emulsified by touch mixing for 1 minute at 40° C. The emulsified mixture was further ultrasonically emulsified for 40 seconds, followed by rapid cooling on ice. Acetone (1.43 ml) was added, and the mixture was centrifuged (5,000 rpm, 5 min, 4° C.) to recover the uncrosslinked particles. The resulting particles were subjected to centrifugal washing (5,000 rpm, 5 min, 4° C.) using acetone. Then, the resulting particles were suspended in an aqueous solution mixture of 30 µl of an aqueous solution of 25% (w/v) of glutaraldehyde and 20 ml of an aqueous solution of 0.1% (w/v) of Tween 80. The suspension was stirred for 40 hours at 4° C. to crosslink the gelatin particles chemically. Then, the resulting particles were recovered by centrifugation (5,000 rpm, 5 min, 4° C.). Then, in order to block the unreacted aldehyde groups, the particles were dispersed in a 0.1 (w/v)% Tween 80 aqueous solution (20 ml) of 100 mM glycine, and the dispersion was stirred for 1 hour at 37° C. After completion of the reaction, the reaction mixture was centrifugally washed with a 0.1 (w/v)% Tween 80 aqueous solution (two times) and with distilled water (three times) to recover the particles. After thorough rinsing with acetone, the particles were air dried. The sizes of the dried particles, and the particles swollen in PB (pH 7.0) for 12 hours at 37° C. were measured from their photomicrographs. Based on the ratio of their sizes, the water content was evaluated as 98.6% by volume (particulate aminated gelatin hydrogel). The average size of the resulting particles in dry state was 100 µm (200 µm in swollen state).

(3) Preparation of DNA Conjugated to Particulate Aminated Gelatin Hydrogel

DNA used was lacZ expression plasmid DNA obtained by inserting lacZ gene of *Escherichia coli* into the EcoRI site of a pCAGGS expression vector having the promoter CAG (chicken β-actin promoter; Gene, 108:193–200, 1991) which has high activity particularly in the muscle (the plasmid will be called pCAGGS-lacZ, or simply referred to as lacZ plasmid; furnished by Miyazaki Laboratory, Molecular Defense Medicine, Osaka University Faculty of Medicine). This DNA was radiolabeled with $TlCl_3$. That is, 5 µl of an Na $^{125}$I solution (740 MBq/ml in 0.1N NaOH aqueous solution, NEN Research Products, DuPont) was mixed with a 0.3 mM $Na_2SO_3$ aqueous solution (2 µl), and the mixture was allowed to stand for 30 minutes at 25° C. To the mixture, 5 µl of a 0.1M $CH_3COONa$-40 mM $CH_3COOH$ mixed solution (pH 5.0) having 5 µg DNA dissolved therein was added. Further, 0.3 ml of a 0.2M $CH_3COONa$-1.0 mM $CH_3COOH$ mixed solution (pH 4.0) having 0.3 mg $TlCl_3$ dissolved therein was added. Then, the resulting mixture was allowed to stand for 40 minutes at 60° C. Then, 0.1 ml of an aqueous solution of 0.1 mM $Na_2SO_3$ was added to the mixed solution, and a 0.1 mM NaCl-50 mM tris-hydrochloric acid solution (pH 7.0) containing 0.9 ml of 1 mM EDTA was further added. The resulting mixture was heated for 30 minutes at 60° C. Upon completion of the reaction, the resulting solution was cooled, and subjected to a PD-10 gel chromatography column (Amersham Pharmacia Biotech) to separate radioiodinated DNA and free radioiodine. Then, 10 µl of an aqueous solution of the radioiodinated DNA was added dropwise to the lyophilized particulate aminated gelatin hydrogel, and the system was allowed to stand for 1 hour at 25° C. During this period, the particles were impregnated with the aqueous solution to obtain a radioiodinated DNA-containing complex.

Example 2

An aqueous solution (end concentration: 10.7 mM) of 1-ethyl-3-(3-dimethylaminopropyl)carbodiimide hydrochloride was added to an aqueous solution of gelatin (end concentration: 5% by weight). Then, the mixture was poured into a plastic petri dish measuring 15 cm×15 cm, and held at 4° C. for 24 hours to carry out a crosslinking reaction. The gelatin used was an alkali-treated gelatin having an isoelectric point of 4.9. After the reaction was completed, the crosslinked gelatin gel was removed from the petri dish to obtain a gelatin sheet of 200 µm in thickness. The resulting sheet was washed thoroughly with water, and then lyophilized. The dry crosslinked gelatin sheet was allowed to stand for 1 hour in an aqueous solution of radioiodinated DNA (lacZ plasmid) prepared in the same manner as in Example 1 to obtain a radioiodinated DNA-containing crosslinked gelatin sheet.

Experimental Example 1

Incorporation of Gene into Particulate Aminated Gelatin Hydrogel

It was confirmed that nucleic acid was taken into a positively-charged water-insoluble biodegradable polymer.

Figure 2:
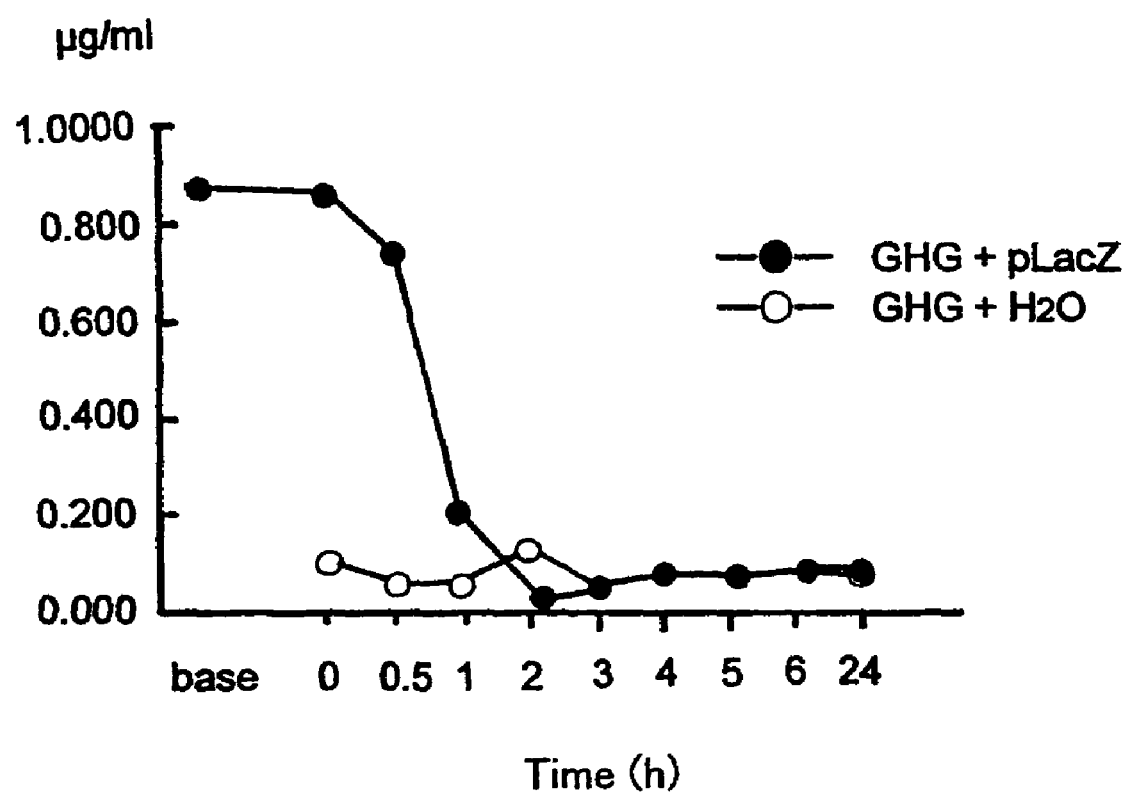
FIG. 2 is a graph showing the process of incorporation of lacZ plasmid into a gelatin hydrogel over time.

An aqueous solution containing lacZ plasmid in a concentration of 500 µg/ml, and the particulate aminated gelatin hydrogel prepared in Example 1-(2) were mixed, and the lacZ plasmid concentration in the aqueous solution was measured over time by the ultraviolet absorbance method (wavelength: 260 nm). As a control, water (containing no lacZ plasmid) was used. The results are shown in FIG. 2.

The lacZ plasmid in the aqueous solution was rapidly incorporated into the particulate aminated gelatin hydrogel within 1 hour (as measured by a decrease in the lacZ plasmid concentration in the aqueous solution). The decline in the lacZ plasmid concentration in the aqueous solution persisted until 24 hours later, demonstrating that the lacZ plasmid continued to be adsorbed to the gelatin hydrogel.

Referential Experimental Example 1

Biodegradability of Particulate Aminated Gelatin Hydrogel

The particulate aminated gelatin hydrogel, a constituent of the nucleic acid-containing complex of the invention, was confirmed to be biodegradable.

An anhydrous benzene solution of $^{125}$I-Bolton-Hunter reagent (NEN-120X, 147 MBq/ml in anhydrous benzene, NEN Research Products, DuPont) was taken in an amount of 0.1 ml into a test tube. Benzene was evaporated by nitrogen gas bubbling. To the test tube, 5 ml of distilled water, in which the particulate aminated gelatin hydrogel prepared in Example 1-(2) was dispersed to a concentration of 10 mg/ml, was added. The mixture was stirred for 12 hours at 4° C. to radioiodinate the gelatin hydrogel. The resulting radioiodinated particulate aminated gelatin hydrogel was centrifugally washed (5,000 rpm, 5 min, 4° C.) with distilled water to remove the $^{125}$I-Bolton-Hunter reagent taking no part in labeling. Finally, the concentration of the particles was adjusted to 0.5 mg/ml with the use of 0.1M phosphate buffered saline (PBS, pH 7.0).

The resulting radioiodinated particulate aminated gelatin hydrogel was administered into the right femoral muscle of ddy mice (female, 6-week-old, purchased from Shimizu Experimental Material Company) at a dose of 0.1 ml per mouse. After a lapse of a predetermined time, the right femoral muscle was resected, and measured for radioactivity. The measured radioactivity was compared with the initial radioactivity administered, to evaluate the residual radioactivity. The experiments were conducted in 3 mice under each of respective experimental conditions. The particulate aminated gelatin hydrogel was degraded over time in vivo, and thus was confirmed to be biodegradable.

Experimental Example 2

Evaluation of In Vivo Survival of DNA

Figure 3:
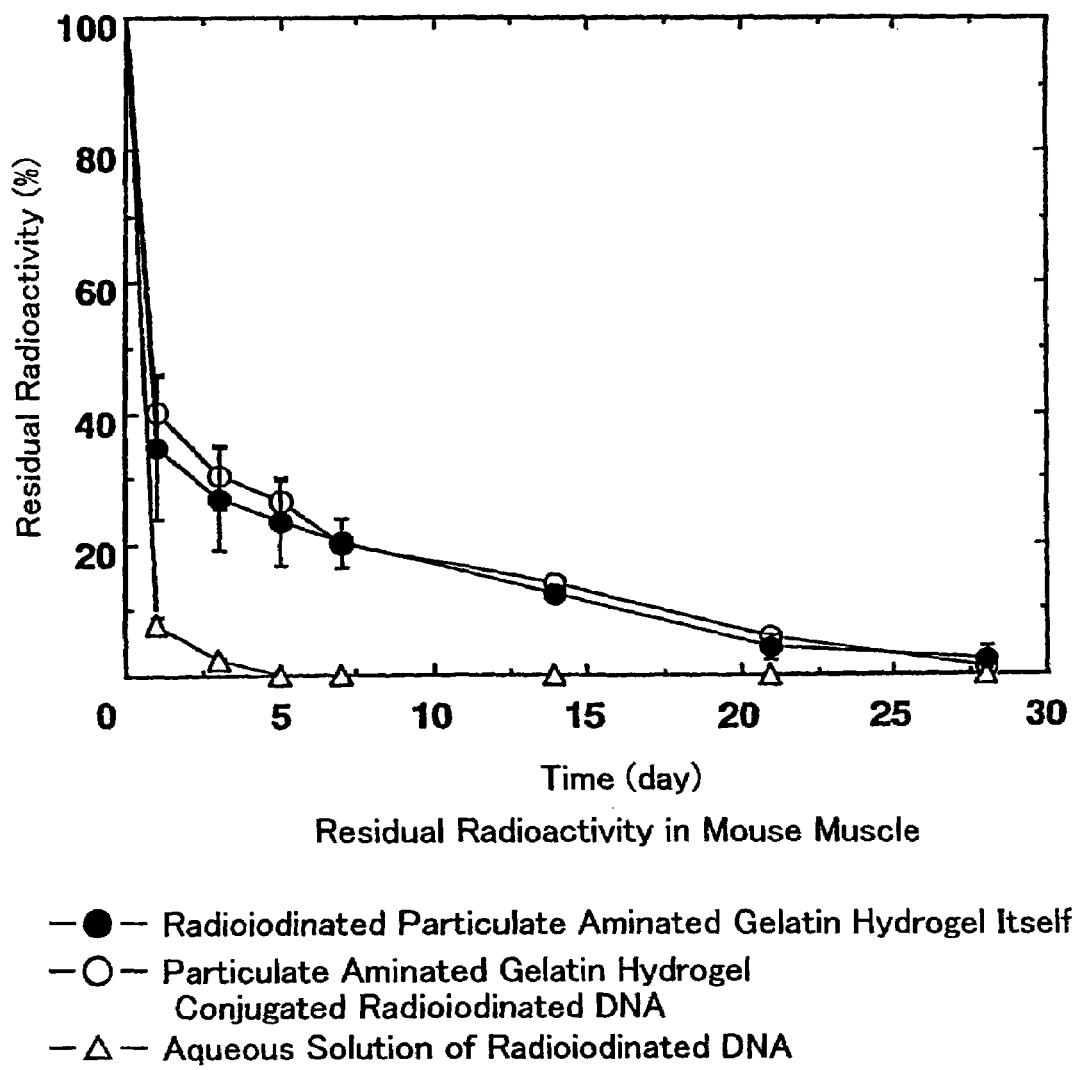
FIG. 3 is a graph showing the results of investigation of in vivo survival of gelatin hydrogel-conjugated plasmid DNA following administration into the right femoral muscle of ddY mice. The survival was confirmed by the residual radioactivity of radioiodine.

A radioiodinated particulate aminated gelatin hydrogel prepared in the same manner as in Referential Experimental Example 1, and the particulate aminated gelatin hydrogel impregnated with radioiodinated DNA prepared in Example 1(3) were each dispersed in 0.1 ml of PBS. Then, the dispersion was administered into the right femoral muscle of ddy mice (female, 6-week-old, purchased from Shimizu Experimental Material Company). As a control, 90 μl of PBS was added to 10 μl of an aqueous solution of radioiodinated DNA, and then the mixture was administered into the right femoral muscle of mice. The number of the experimental animals was three for each of the experimental conditions, and the residual radioactivity was expressed as the mean value ± standard deviation. The results are shown in FIG. 3.

The residual radioactivity of the gelatin particles gradually decreased over time, thus showing that the particles were degraded in vivo, in other words, they were biodegradable (-●-). The residual radioactivity of DNA impregnated into the gelatin hydrogel also decreased with the passage of time, and its profile over time was the same as that of the residual radioactivity of the particulate aminated gelatin hydrogel itself (-○-). This is proof that DNA was released in a sustained manner from the particles as the particles were degraded. When DNA was administered as an aqueous solution, the residual radioactivity rapidly decreased (-△-). This finding shows that DNA was rapidly excreted or metabolized without being retained at the site of administration.

Experimental Example 3

Gene Expression of Particulate Aminated Gelatin Hydrogel Conjugated DNA

Figure 4:
FIG. 4 shows micrographs demonstrating the expression of lacZ gene in a rabbit lower limb ischemic model two weeks after administration of particulate aminated gelatin hydrogel-conjugated lacZ plasmid.
Figure 4:
Figure 4:
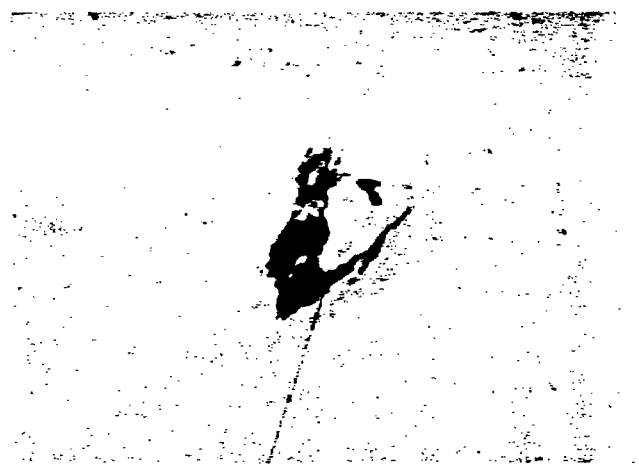

A rabbit's femoral artery was removed to prepare a lower limb ischemic model. Ten days later, lacZ plasmid was administered into the muscle of the ischemic site. At 2 weeks after administration, the muscular tissue of the ischemic part was stained for LacZ to investigate the expression of the gene. The results are shown in FIGS. 4A to 4C.

The investigations were carried out for the particulate aminated gelatin hydrogel (diameter 200 μm when swollen) conjugated lacZ plasmid prepared in Example 1(3) (500 μg as the amount of lacZ plasmid: FIG. 4A), and naked lacZ plasmid not conjugated to the particulate aminated gelatin hydrogel (500 μg, control: FIG. 4B). The investigation was also conducted for the administration of the particulate aminated gelatin hydrogel conjugated lacZ plasmid with the amount of the lacZ plasmid being decreased to 1/10 (50 μg as the amount of lacZ plasmid: FIG. 4C).

Staining of lacZ was performed in the following manner:

1. Fix the sample in a 37% formaldehyde-25% glutaraldehyde mixed solution for 5 minutes at 4° C.

2. Wash with PBS (3 times).

3. Stain with a staining solution (1 mg/ml X-gal, 5 mM potassium hexacyanoferrate(III), 5 mM potassium hexacyanoferrate(II), 1M magnesium chloride).

Compared with the administration of lacZ plasmid alone, lacZ plasmid bound to the particulate aminated gelatin hydrogel showed more extensive expression of the gene (comparison of A with B).

The lacZ plasmid bound to the particulate aminated gelatin hydrogel also showed significant expression of the gene even when its dose was decreased to 1/10.

Referential Experimental Example 2

Gene Expression Using Adenovirus Vector

Gene transfer using an adenovirus vector was investigated in a rabbit's lower limb ischemic model in the same manner as in Experimental Example 3.

An adenovirus vector incorporating 1×10$^9$ pfu of lacZ gene (furnished by Saito Laboratory, The Institute of Medical Science, The University of Tokyo) was administered. Three days after administration, the expression of lacZ gene was stronger than by the administration of lacZ plasmid alone and the administration of lacZ plasmid bound to the particulate aminated gelatin hydrogel (FIG. 5A). However, the gene expression significantly declined at 2 weeks after administration (FIG. 5B).

Experimental Example 4

Vasculogenesis in Rabbit's Lower Limb Ischemic Model

Vasculogenesis by the administration of fibroblast growth factor FGF4/HST1 plasmid was investigated in a rabbit lower limb ischemic mod 1 as in Experimental Example 3.

Particulate aminated gelatin hydrogel conjugated FGF4/HST1 plasmid was prepared in the same manner as in Example 1, except that the nucleic acid used was FGF4/HST1 plasmid (500 μg or 5 μg). As the plasmid, there was used FGF4/HST1 expression plasmid DNA (hereinafter referred to simply as FGF4/HST1 plasmid) obtained by inserting FGF4/HST1 gene (SEQ. ID No. 1 of the sequence listing) into the HindIII site of pRc/CMV2 vector (INVITORGEN).

As controls, naked FGF4/HST1 plasmid (500 μg), and lacZ plasmid (500 μg) conjugated to the same gelatin hydrogel were used.

Ten days after preparation of the lower limb ischemic model, the various plasmids of the above embodiments were each intramuscularly injected into the ischemic site. At 2 weeks after administration, angiography of neogenetic blood vessels (radiography) was performed. The results are shown in FIGS. 6A to 6D.

Figure 5:
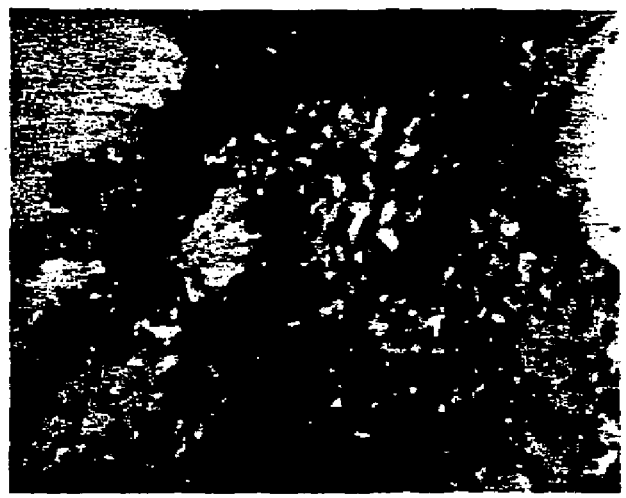
FIG. 5 shows micrographs demonstrating the expression of lacZ gene in a rabbit lower limb ischemic model after administration of lacZ gene with the use of an adenovirus vector.
Figure 5:
Figure 6A:
FIGS. 6A–D show radiographs demonstrating vasculogenesis in a rabbit lower limb ischemic model after administration of FGF4/HST1 plasmid.
Figure 6B:
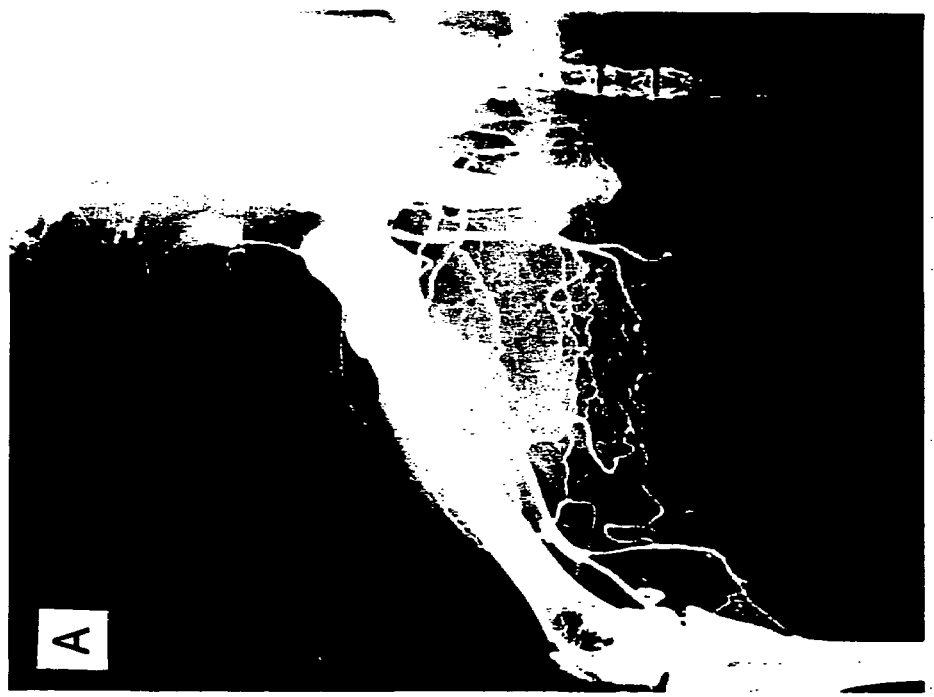
Figure 6D:
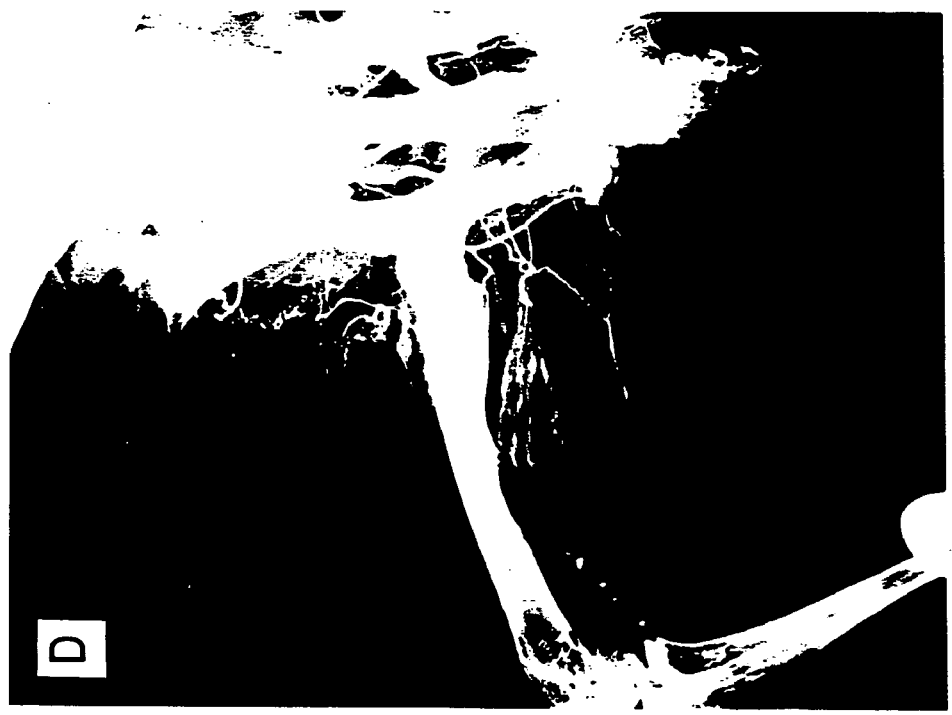
Figure 6C:
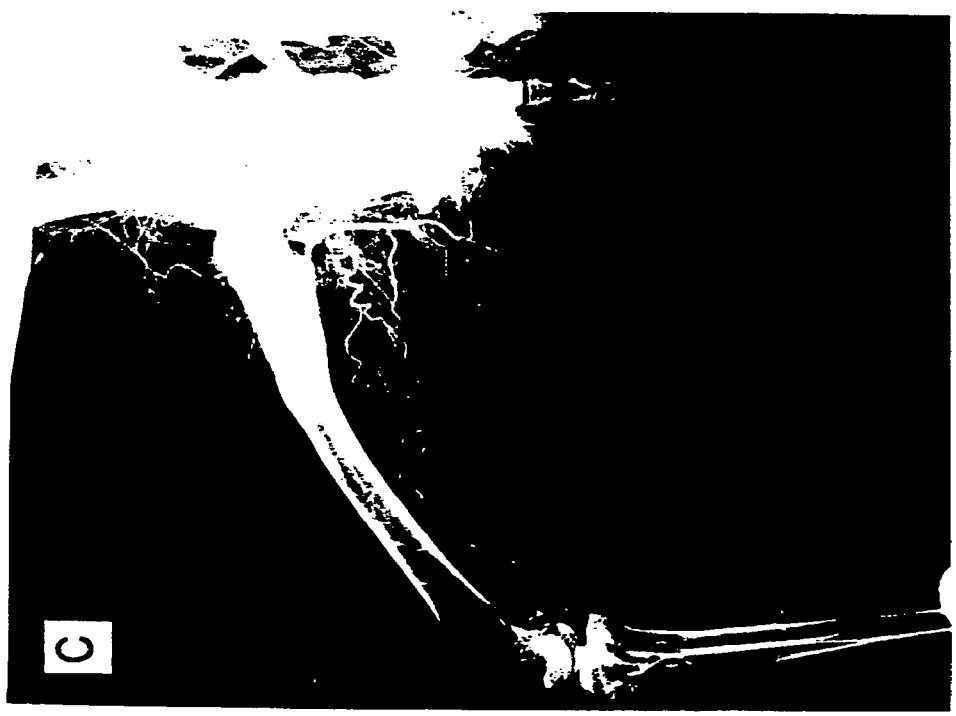

FIGS. 6A and 6B show the results for the administration of the particulate aminated gelatin hydrogel-conjugated FGF4/HST1 plasmid (amount of FGF4/HST1 plasmid: 500 μg in FIG. 6A, 5 μg in FIG. 6B). FIG. 6C show the results for the administration of the particulate aminated gelatin hydrogel-conjugated lacZ plasmid (500 μg, control). FIG. 6D show the results for the administration of the naked FGF4/HST1 plasmid (500 μg, control). The administration of FGF4/HST1 plasmid conjugated to the particulate aminated gelatin hydrogel resulted in the new growth of more blood vessels than the administration of the plasmid in its naked form. Thus, the functional expression of FGF4/HST1 plasmid was found to be enhanced (comparisons of FIG. 6A with FIGS. 6C and 6D). This effect was observed even when its dose was decreased to 1/100 (FIG. 6B). Furthermore, it became possible for FGF4/HST1 plasmid to function locally with high efficiency when administered in a form conjugated to the gelatin hydrogel, rather than in a naked form.

Experiments using $VEGF_{165}$ plasmid (500 μg) instead of FGF4/HST1 plasmid gave similar results. $VEGF_{165}$ plasmid was provided by Prof. Shibuya of the University of Tokyo. This plasmid is obtained by inserting VEGF165 gene into the XhoI site of a pCAGGS expression vector (Shibuya M, Adv. Cancer Res., 67, 281–316, 1995).

Experimental Example 5

Gene Transfer to Rabbit Arterial Wall (1) lacZ Plasmid

Figure 7:
FIG. 7 is a micrograph showing lacZ expression in macrophages in a rabbit arterial wall. Macrophages having expressed lacZ are present (arrows).

The thin sheet of dry crosslinked gelatin prepared in Experimental Example 2 was mounted on a stainless stent (Synthesis; Cardio Vascular Dynamics, Inc.). A lacZ plasmid solution (5 to 10 μg/μl) was added dropwise to the thin sheet of crosslinked gelatin, with the dropwise addition being repeated for 2 hours to avoid drying (total amount added dropwise: 50 to 100 μl). By this measure, the crosslinked gelatin and the lacZ plasmid were conjugated. The stent coated with this crosslinked gelatin was implanted into a rabbit's iliac artery. Five days later, the iliac artery was withdrawn, embedded in Tissue-Tek(R) O.C.T. Compound, and fixed in liquid nitrogen. This sample was stored at −80° C. until use. Slices were prepared from the fixed sample, and subjected to hematoxylin-eosin (HE) staining, DAB (diaminobenzenezidene), and Xgal staining. the results are shown in FIG. 7.

In the layer outward of the vascular smooth muscle tunica, the expression of lacZ was observed, confirming the uptake of the plasmid by macrophages and the expression of the plasmid.

(2) VEGF165 Plasmid

In the same manner as described in (1) above, a solution of 1 to 2 μg/μl of VEGF165 plasmid was added dropwise in an amount of 50 to 100 μl to the thin sheet of crosslinked gelatin. The expression of this plasmid was confirmed by immunohistochemistry staining (anti-human VEGF IgG fraction (Austral Biologicals) was used as a primary antibody).

Experimental Example 6

Study of Maturity of Neogenetic Vasoganglia by Radiation Microvascular Angiography (1) Administration of Plasmid An aqueous solution containing 500 μg of naked $VEGF_{165}$ plasmid unconjugated to crosslinked gelatin was administered visually into a diseased lower limb femoral muscle of a rabbit having lower limb ischemia (as in Experimental Example 3).

Separately, physiological saline containing 500 μg of $VEGF_{165}$ plasmid conjugated to 4 mg of particulate crosslinked gelatin having a diameter of about 200 μm was administered visually into a diseased lower limb femoral muscle of a rabbit having lower limb ischemia.

(2) Adenosine Loading

Adenosine was administered to the abdominal aorta at a dose of 100 μg/kg/min.

(3) Measurements and Results

Figure 8:
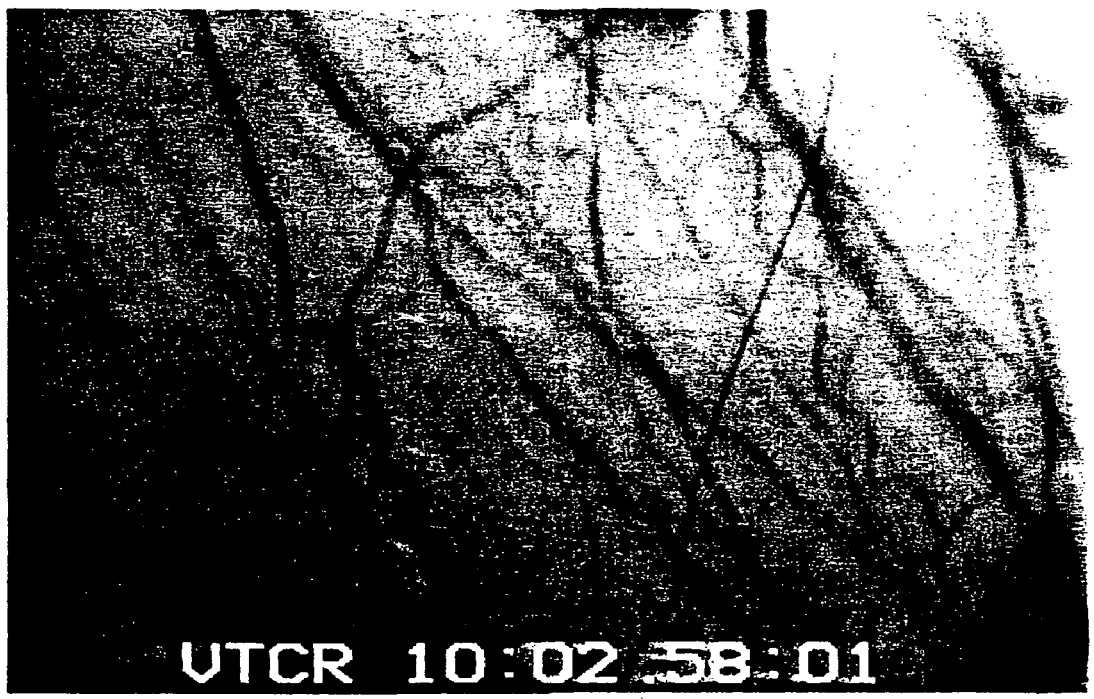
FIG. 8 shows photographs of halftone images appearing on a display showing the blood vessel density at baseline (top) and during vasodilation (adenosine treatment) (bottom), as obtained by radiation microvascular angiography. The results after administration of naked $VEGF_{165}$ plasmid are presented.
Figure 8:
Figure 9:
FIG. 9 is photographs of halftone images appearing on a display showing the blood vessel density at baseline (top) and during vasodilation (adenosine treatment) (bottom), as obtained by radiation microvascular angiography. The results after administration of gelatin hydrogel-conjugated $VEGF_{165}$ plasmid are presented.
Figure 9:

The maturity of neogenetic vasoganglia was measured in the naked $VEGF_{165}$ plasmid group and the gelatin hydrogel conjugated $VEGF_{165}$ plasmid group by radiation microvascular angiography (space resolution 25 microns). The results of the naked $VEGF_{165}$ plasmid treatment are shown in FIG. 8, while the results of the gelatin hydrogel conjugated $VEGF_{165}$ plasmid treatment are shown in FIG. 9. In the naked $VEGF_{165}$ plasmid treated group, the blood vessel density following adenosine loading (during vasodilation) decreased compared with the baseline (no loading of adenosine). In the gelatin hydrogel conjugated $VEGF_{165}$ plasmid treated group, the blood vessel density following adenosine loading clearly increased. These findings show that in the gelatin hydrogel conjugated $VEGF_{165}$ plasmid group, the bloodstream at the baseline was controlled to a low level, and vasodilation reserve capacity was mobilized during adenosine loading. In the naked $VEGF_{165}$ plasmid group, on the other hand, the bloodstream at the baseline was not controlled to a low level, and there was no vasodilation reserve capacity to be mobilized during adenosine loading. Maturity of the blood vessel system, such as vascular smooth muscle and neural or humoral regulation mechanism in neogenetic blood vessels, is indispensable to the control of the bloodstream and vasodilation during adenosine loading. The administration of the gelatin hydrogel conjugated $VEGF_{165}$ plasmid has been found to be able to achieve these states.

Referential Example 3

Uptake of Nucleic Acid-Containing Complex by Macrophages

Figure 10:
FIG. 10 shows micrographs demonstrating macrophages having taken in crosslinked gelatin particles-GFP plasmid.
Figure 10:
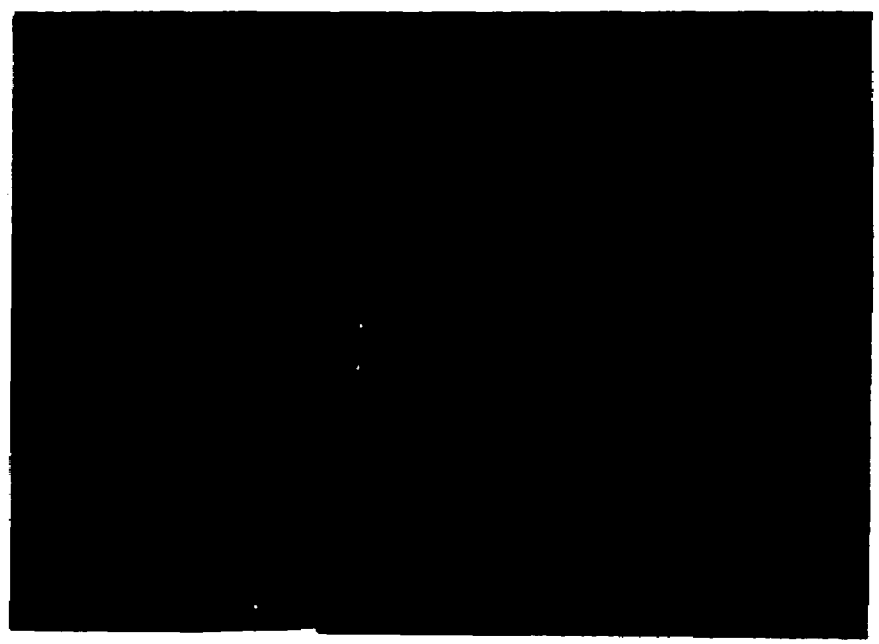

Macrophages incorporating a nucleic acid-containing complex were prepared in vitro. Thioglycolate was injected intraperitoneally into mice, and macrophages were taken 4 days later. Separately, 100 μg of 2 mg green fluorescence protein (GFP) plasmid (Prasher D C et al. Gene, 111, 229–233, 1992; Heim R et al. Nature, 373, 663–664, 1995) was conjugated to the crosslinked gelatin particles prepared in Example 1. The plasmid was prepared by inserting cDNA for GFP (purchased from Clontech) into the multicloning site of HIV-CS vector. The crosslinked gelatin particles-GFP plasmid was mixed with the macrophages collected, and the mixture was cultured in PBS for 4 days at 33° C. After four days of culture, the fluorescence of GFP was checked with a fluorescence microscope and a fluorescence activated cell sorter (FACS). The results are shown in FIG. 10. Fluorescence was observed in the macrophages, confirming the uptake of the crosslinked gelatin particles-GFP. Similar results were confirmed in experiments using the crosslinked gelatin particles immersed in an eosin staining solution (confirmation of eosin particles in macrophages).

Experimental Example 7

Gene Transfer to Dendritic Cells and Induction of CTL to Particular Antigen

Dendritic cells (DC) separated from human peripheral blood were administered GFP plasmid, and examined for antigen presenting ability.

Particulate aminated gelatin hydrogel conjugated GFP plasmid was prepared in the same manner as in Example 1, except that the nucleic acid used was GFP plasmid (described earlier; 20 μg).

Figure 11:
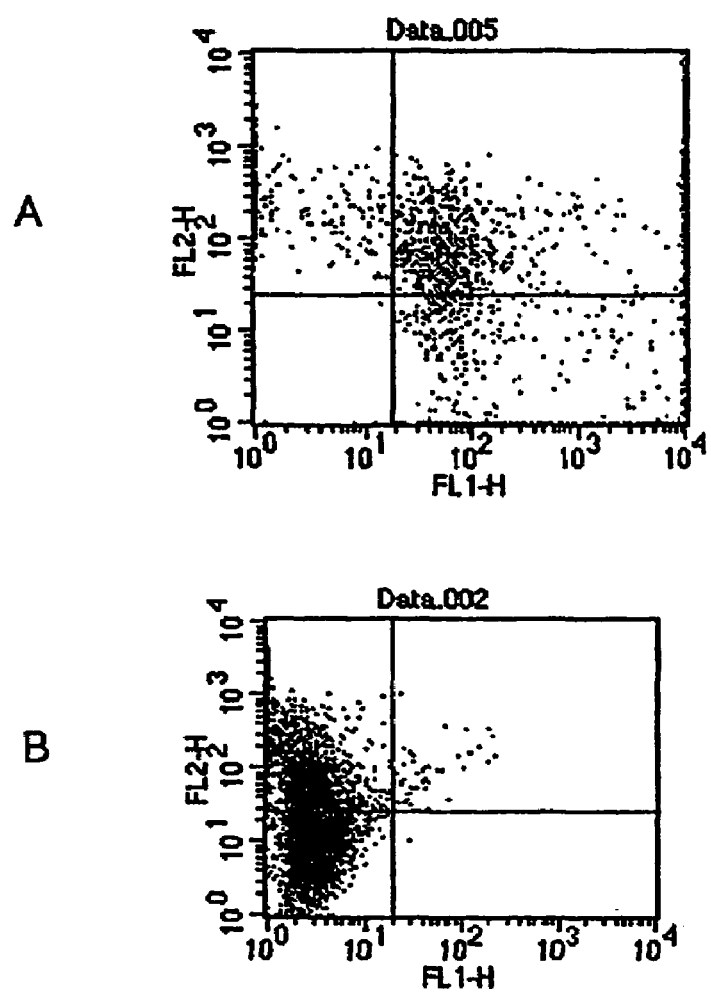
FIG. 11 shows views demonstrating the results of FACS analysis of the efficiency of gene transfer into human dendritic cells (DC).

A CD 14 positive fraction was obtained from monocytes of healthy subjects, and added together with GM-CSF and IL-4 to pooled human serum/RPMI medium to induce DC. After a lapse of 4 to 6 days, the particulate aminated gelatin hydrogel conjugated GFP plasmid was added to DC. The mixture was allowed to stand for 60 minutes, and the gelatin hydrogel was removed, then the cells were further cultured for 3 days. The DC after culture were stained with CD1a-PE and CD83-PE as DC markers, and the efficiency of gene transfer to the DC was investigated by FACS analysis. The results are shown in FIGS. 11A and 11B. As a control, naked GFP plasmid (20 μg) was used. The gene transfer efficiency was 77%.

A similarly high gene transfer efficiency was obtained when WT1 plasmid (Call K M, et al. Cell, 60, 509–520, 1990) was used instead of GFP plasmid.

Whether DC having the WT1 gene transferred thereto has the ability of cell presentation for a gene product was measured by CTL induction capacity. T lymphocytes of the same healthy subjects having induced DC were co-cultured with DC which carried the WT1 gene to obtain activated T lymphocytes. These cells were labeled with $^{51}Cr$ to form target cells. Using these target cells, CTL assay was performed. CTL was induced to the transferred WT1, showing the antigen presenting capability of the WT1 gene transformed DC.

According to the invention, as described above, a stable firm binding between the negative charge of a nucleic acid and the positive charge of a biodegradable polymer leads to the formation of a complex. Release of the nucleic acid is controlled by the in vivo degradation of the biodegradable polymer. Thus, more accurate control of the rate of release can be achieved, in comparison with slow release by simple diffusion as observed with conventional slow release preparations, and transient release of nucleic acid by the use of a water soluble biodegradable polymer. Moreover, a sustained release over a longer time is improved.

With the nucleic acid-containing complex of the invention, this complex is insoluble, and the nucleic acid is protected from degradation in vivo. Thus, the nucleic acid can be maintained in a sufficiently active state until the nucleic acid arrives at a site where its function either by expression of a gene or by direct action of the enclosed nucleic acid should be exhibited. Thus, the local expression and/or action of the nucleic acid can be achieved. That is, gene therapy restricted to the site requiring treatment can be achieved.

Furthermore, the rate of release of the nucleic acid is controlled by the type of the biodegradable polymer used, and the balance between the positive charge and the negative charge. Thus, the rate of release is constant, and particular attention need not be paid to its shape in formulating the complex.

Releasing a nucleic acid locally, consistently and persistently for a long period is particularly useful in the field of gene therapy. As the desired gene can be administered for a long term to a site or a living organism requiring therapy, there will be an increased need for adjusting the timing of gene transfer, and the timing of introducing a nucleic acid most preferred for gene expression and functional expression.

According to the invention, the desired effect can be expected with the amount of nucleic acid which is about 1/10 to 1/100 of the usual dose. That is, the invention acts to enhance the effective activity of the nucleic acid. This action is preferred from the aspects that the gene may be administered at a low dose, and the collateral effect of the gene on other sites than the desired site can be diminished.

Another embodiment of the nucleic acid-containing complex of the invention is to provide a new method capable of achieving target site-specific functional expression of nucleic acid by use of the phagocytosis of phagocytes such as macrophages, and the migration of the phagocytes. This method makes safer and easier gene therapy possible.

The invention claimed is:

1. A nucleic acid-containing complex comprising a nucleic acid and a positively-charged water-insoluble biodegradable polymer,
wherein said positively-charged water-insoluble biodegradable polymer is crosslinked prior to complexation with said nucleic acid;
wherein said nucleic acid can be released by degradation of said biodegradable polymer;
wherein said nucleic acid is a fibroblast growth factor gene comprising SEQ ID NO:1.

2. A nucleic acid-containing complex comprising a nucleic acid and a positively-charged water-insoluble biodegradable polymer having an introduced positively-charged group,
wherein said positively-charged water-insoluble biodegradable polymer having an introduced positively-charged group is crosslinked prior to complexation with said nucleic acid;
wherein said nucleic acid is a fibroblast growth factor gene comprising SEQ ID NO:1.

* * * * *

SEQUENCE LISTING

<160> NUMBER OF SEQ ID NOS: 1

<210> SEQ ID NO 1
<211> LENGTH: 3149
<212> TYPE: DNA
<213> ORGANISM: Homo sapiens

<400> SEQUENCE: 1

```
gcactgctcc tcagagtccc agctccagcc gcgcgctttc cgcccggctc gccgctccat      60
gcagccgggg tagagcccgg cgcccggggg ccccgtcgct tgcctcccgc acctcctcgg     120
ttgcgcactc ctgcccgagg tcggccgtgc gctcccgcgg gacgccacag gcgcagctct     180
```

-continued

```
gcccccccagc ttcccgggcg cactgaccgc ctgaccgacg cacggccctc gggccgggat    240 gtcgggccc  gggacggccg cggtagcgct gctcccggcg gtcctgctgg ccttgctggc    300
gccctgggcg gccgagggg cgccgccgc acccactgca cccaacggca cgctggaggc     360
cgagctggag cgccgctggg agagcctggt ggcgctctcg ttggcgcgcc tgccggtggc    420
agcgcagccc aaggaggcgg ccgtccagag cggcgccggc gactacctgc tgggcatcaa    480
gcggctgcgg cggctctact gcaacgtggg catcggcttc cacctccagg cgctccccga    540
cggccgcatc ggcggcgcgc acgcggacac ccgcgacagc ctgctggagc tctcgcccgt    600 ggagcgggc  gtggtgagca tcttcggcgt ggccagccgg ttcttcgtgg ccatgagcag    660
caagggcaag ctctatggct cgcccttctt caccgatgag tgcacgttca aggagattct    720
ccttcccaac aactacaacg cctacgagtc ctacaagtac cccggcatgt tcatcgccct    780
gagcaagaat gggaagacca agaagggaa ccgagtgtcg cccaccatga aggtcaccca    840
cttcctcccc aggctgtgac cctccagagg acccttgcct cagcctcggg aagcccctgg    900
gagggcagtg ccgagagtca ccttggtgca ctttcttcgg atgaagagtt taatgcaaga    960
gtaggtgtaa gatatttaaa ttaattattt aaatgtgtat atattgccac caaattattt   1020
atagttctgc gggtgtgttt tttaattttc tgggggaaa aaaagacaaa acaaaaaacc    1080
aactctgact tttctggtgc aacagtggag aatcttacca ttggatttct ttaacttgtc   1140
aaaagttgtc acgagtgtgc tgctattctg tgttttaaaa aaggtgaca ttggattccg    1200 atgtcatccc ctgtagtatg gcgtggagca tctctgtctg gaaaggcccg cctgaggctt   1260
gggcagccag ttcagggagc tcccaggctt ggctctcggc tagcatcctc agaggcccac   1320 tcccttttgtg ccctgttgct attaatcggg acatatcggt ttacttcggg tacagaaagt  1380
gcggtgttga agtcctcgct gccactctgt ttttagatct gccaagactg acctttgaac   1440
tttcctgtag tcaatcttcc tcgatctacc agatgggaga gacccttgga caactttata   1500
aactcctgtt tgcctttttt ggatcagcga cagcccccat cgctgtgact attggggaaa    1560
agacgaagct ctttcataaa ttccatggag aggaatcaat atcccactgg aaggctagaa   1620
atggacaaga tagtgtattt gcaatcacaa acaaaaccct agtgatgaaa ataatttgt    1680 gatggcagat gcttctgatg gtgtgataga atatgtttttt gaaaacaaac catcgaaccc   1740
cccgccccac ccccaaaacg ggcttccctg tgtttaggga gctttgggct agaactagct   1800
acgattttta ggtgaaatgt ccttgtaatt gtacaaagca cttggtgcag tgtttgcgtg   1860
gagcagcctg ctgctttctg atgcattccc tgtttaagtg cgtttaacat ctacctcaca    1920
agccctgaaa ccccaggcaa aacccacaga aagctcatac ccggtgcagg agtttgccat   1980
cccaagtggc tttttttcca tatgtagcca aaaaggattg cagatagcgt cggtgcgtcc    2040
cattcgaacc ttgtcacgtt tgagctatct ttaccctgtg atttacttt  agtaagggtg   2100 atcatggtga aaatatttgc agacagctgt tacagtacac tatatggtca ccaagtaacc   2160
ttatattttt cttatatat tttacaaatg taaccctgt cattgaagca accgtggaag     2220
aggcagggtc ggtgatgttt aaaaaaagtt ccgaggtgat ggcaaacatt taattttaat   2280
gaatgacttt ttagagttta tacaaaatga ccttagcttg ctaccagaaa tgctccgaat   2340
gtttcgtcaa gactttaata ctctcctagg atgtttctga actgtctccc gaattaactt   2400
tatgggagtc tacagacagc aagactggaa aatctgattg gagttttgt ctttcacatt    2460 ccttttgaaa actctttgtt cgaatgcaaa tcatcgactt aaaatactat tcttaaccaa   2520
```

```
ggcctggaag aaagaagaca cttgcaaagc cgctaagaca ggaccacaca tcttaaactg    2580
ctgttcctac catgcactaa actgttttta agttttaaac cacaccctag gctccaggag    2640
tgttcaggaa agatggtgtt tgtaggtctc catgctgttt ggcgttgggg ggtgtggagg    2700
gatcatccgt cgactttctg aattttaatg tattcactta gtaacaaacc atgattgtct    2760
taaatgcctt aaattattat gagatttctt gtctcagagc ccaatcagat tgtcaggaat    2820
taacatgtgt taggtttgat caccettgac cacttcttat agatatttct tcaacaaatc    2880
atgtgtgatg cctgtaggaa cacaactgta cctttaaaat attgttttca tattgctgtg    2940
atggggattc gaggttcctg tatgtgccac tgttttcaga atctgtagtt ttatacaggt    3000
gccgaccctc gttgtgatgt atgtgctgtg cacattgaca tgctgaccga caatgataag    3060
cgtttatcgt gtataaaaag acaccactgg actggatgta cacaactggg aaaggaatta    3120
aaagctatta aaattgtgcc ttgaaatgc                                      3149
```